US00PP26464P3

(12) United States Plant Patent
Schoone

(10) Patent No.: US PP26,464 P3
(45) Date of Patent: Mar. 8, 2016

(54) ***PHALAENOPSIS* ORCHID PLANT NAMED 'FLOR239431'**

(50) Latin Name: *Phalaenopsis hybrida*
Varietal Denomination: FLOR239431

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 175 days.

(21) Appl. No.: 13/998,014

(22) Filed: Sep. 24, 2013

(65) Prior Publication Data

US 2014/0090129 P1 Mar. 27, 2014

Related U.S. Application Data

(60) Provisional application No. 61/704,878, filed on Sep. 24, 2012.

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

U.S. PATENT DOCUMENTS

PP24,365 P3 * 4/2014 Schoone ..... Plt./311

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'FLOR239431' particularly characterized by flowers which are red/purple with yellow/green and have a purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'FLOR239431'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'FLOR239431'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves, may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'FLOR239431' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'FLOR239431' originated from a cross made by the inventor in 2000 in Strengweg, Heemskerk, The Netherlands. The female or seed parent is the *Phalaenopsis* cultivar designated 'Fortune Buddha', unpatented. The male or pollen parent is the *Phalaenopsis* cultivar designated 'Irene', unpatented. The new *Phalaenopsis* 'FLOR239431' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture (mericloning) was first performed in July, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'FLOR239431', which in combination distinguish this *Phalaenopsis* as a new and distinct cultivar:

1. flowers which are red/purple with yellow/green and have a purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'FLOR239431', the female parent 'Fortune Buddha' has yellow with red/purple colored flowers whereas the flowers of 'FLOR239431' are yellow/green instead of yellow and have more red/purple than 'Fortune Buddha'. The male parent 'Irene' has orange/red colored flowers, whereas the flowers of 'FLOR239431' are yellow/green with red/purple .

Presently, the commercial cultivar to which 'FLOR239431' can be meaningfully compared is 'Irene's Fire' (unpatented). The plants are both about the same size and also the flowers are about the same size. However, the flowers of 'Irene's Fire' have more green/yellow than the flowers of 'FLOR239431' and they have red/purple stripes, whereas the flowers of 'FLOR239431' have red/purple spots. Also the labellum of 'Irene's Fire' is darker purple than the labellum of 'FLOR239431'.

BRIEF DESCRIPTION OF THE PHOTOGRAPHS

The accompanying photographs illustrate the overall appearance of the new *Phalaenopsis* 'FLOR239431' showing the colors as true as is reasonably possible with colored reproductions of this type. Colors in the photographs may differ slightly from the color values cited in the detailed botanical description, which accurately describe the color of 'FLOR239431'.

DETAILED BOTANICAL DESCRIPTION

Figure 1:
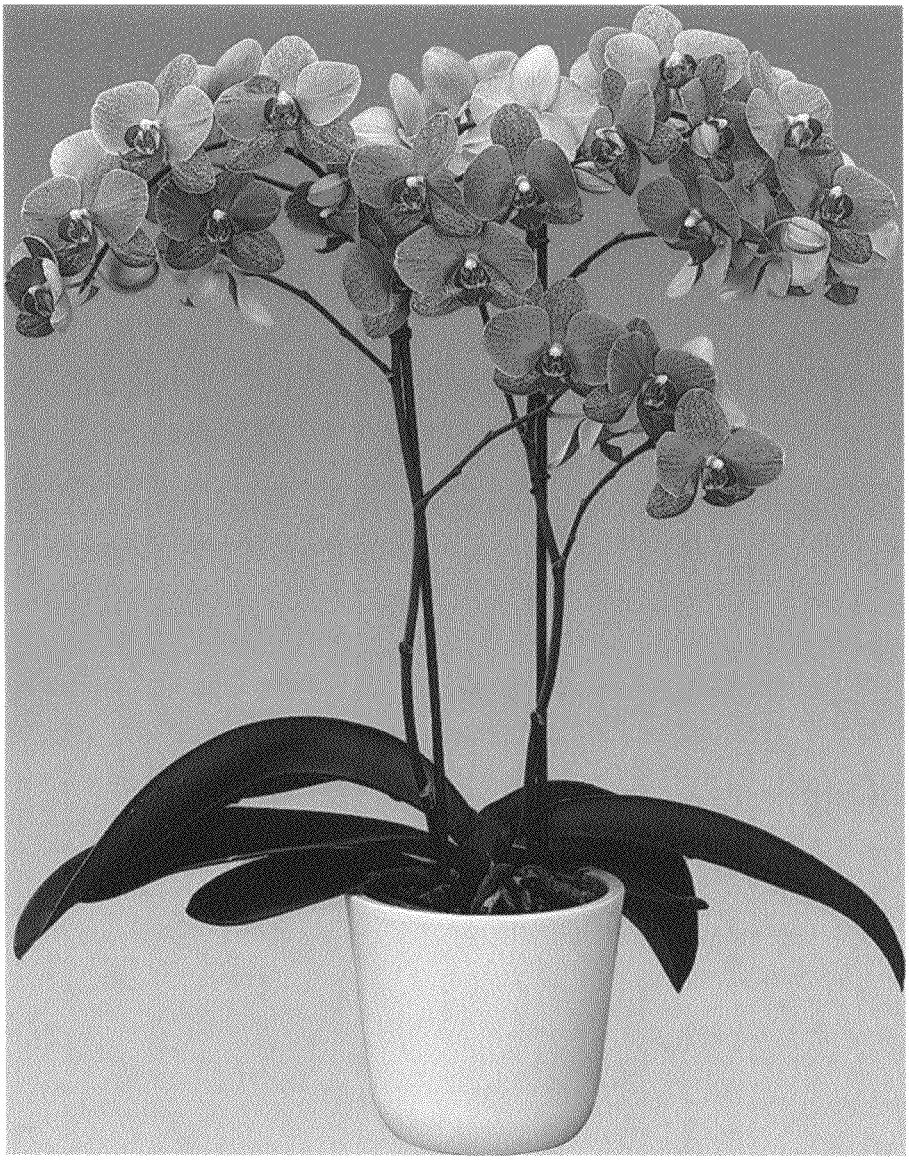
FIG. 1 shows a side view perspective of a typical flowering plant of 'FLOR239431' in a 12 cm pot, at 16 months of age.

The new *Phalaenopsis* cultivar 'FLOR239431' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'FLOR239431' as grown in a greenhouse in Strengweg, Heemskerk, The Netherlands, under conditions which closely approximate those generally used in commercial practice. Initially, the ideal temperature to grow plants of 'FLOR239431' is 27° C. during the day and at night. Then, during the flowering phase of 'FLOR239431', the ideal growing temperature is 20-22° C. during the day and 18° C. at night. Light levels for growing 'FLOR239431' are a minimum of 5,000 lux and a maximum of 10,000 lux. A balanced fertilizer with level of 200 ppm N, 87 ppm P, 168 ppm K is applied. Duration of growth of 'FLOR239431' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'FLOR239431' plants described is 12 months after potting.

Classification:

*Botanical.*—*Phalaenopsis hybrida.*

Parentage:

*Female or seed parent.*—*Phalaenopsis* cultivar designated 'Fortune Buddha', unpatented.

*Male or pollen parent.*—*Phalaenopsis* cultivar designated 'Irene', unpatented.

Propagation:

*Type.*—Tissue culture (mericloning).

*Rooting habit and description.*—Fleshy; approximately 3 mm-7 mm wide and grey/green in color (RHS 190B); freely branching. It takes 12 weeks for plants growing in tissue culture to initiate roots.

Plant:

*Size at maturity.*—Height (from bottom of pot to highest flower): about 50 to 60 cm. Spread: about 50 cm.

*Growth habit.*—Normal; green and purple leaves (RHS 143B, N79A and 137A) and a relatively large raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant.*—About 5 to 8 leaves are produced before flowering.

*Arrangement and attachment.*—Half up/horizontal and on two sides.

*Overall shape of leaf.*—Oval, the tip is blunt and asymmetric.

*Texture* (*upper & underside*).—Smooth and leathery.

*Pubescence.*—None.

*Mature leaf length.*—About 15 to 22 cm.

*Mature leaf width.*—About 6 to 8 cm.

*Mature leaf thickness.*—About 2 mm.

*Mature leaf color* (*upper surface*).—From base green (RHS 143B) and purple (RHS N79A) which runs into green (RHS 137A).

*Mature leaf color* (*under surface*).—Green (RHS 138A) with purple (RHS N79A).

*Leaf base.*—Acute.

*Margin.*—Entire.

*Venation.*—Pattern: parallel. Color of midvein upper surface: green (RHS 137A). Under surface: RHS N79A.

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 2. Number of flowers per raceme: about 10 to 22. Length: about 40 to 50 cm.

*Peduncle.*—Diameter: about 4 to 6 mm. Strength: strong. Aspect: upright. Texture: glabrous and smooth. Color: brown (RHS N200A) with green spots (RHS 143B).

*Buds.*—Height (from base to tip): about 20 mm. Diameter (at midpoint): about 17 mm. Shape: oval/egg-shaped. Color: yellow/green (RHS 145A) with a red/purple haze (RHS 71A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
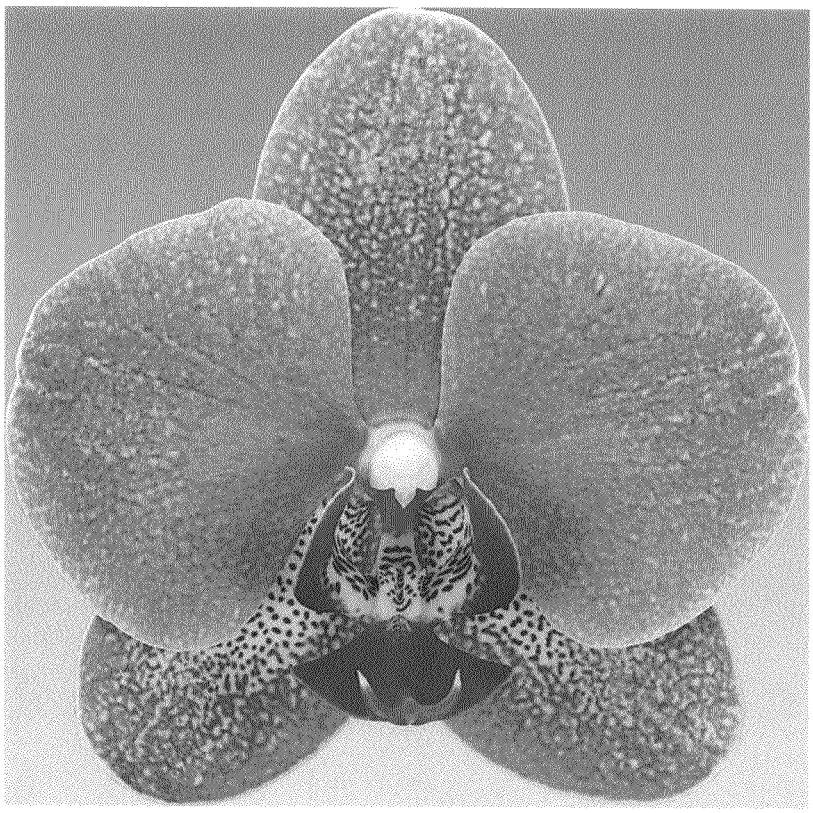
FIG. 2 shows a close-up view of a typical flower of 'FLOR239431'.
Figure 3:
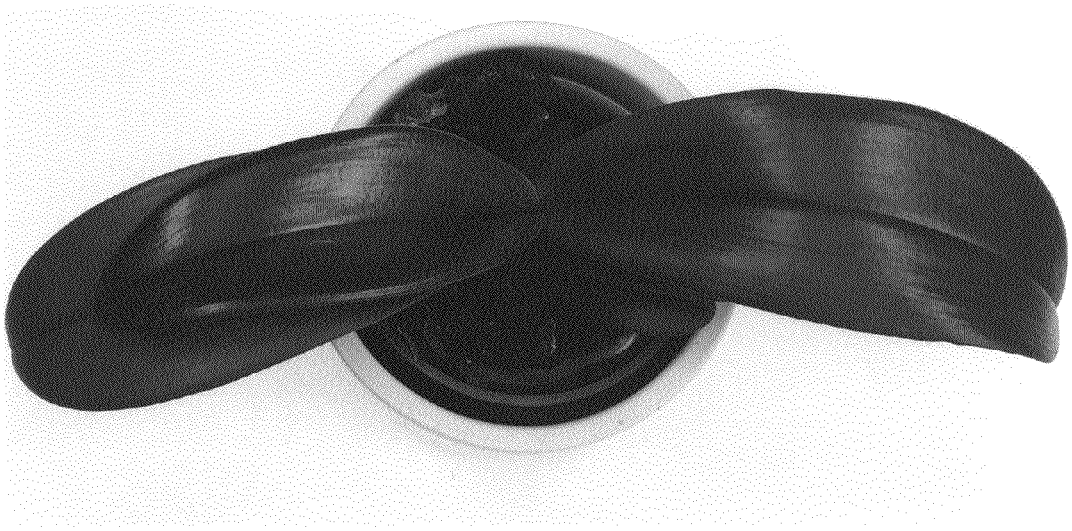
FIG. 3 shows a close-up view of the typical leaves of 'FLOR239431'.

*Flower.*—Rate of opening: Flowers fully opened about 2 to 3 days after petal and sepal separation. Orientation at opening: slanted upward and outward. Shape: Typical shape of *Phalaenopsis*, see FIG. 2. Size (of single bloom): Height: about 5 to 7 cm. Diameter: about 6 to 9 cm. Quantity and arrangement: Three petals and three sepals that are trimerous and arranged in 2 overlapping whorls. Inner whorl of 3 petals is comprised of 2 lateral petals and a labellum. Petals are more pronounced than sepals.

*Petals.*—2 lateral petals: Overall shape: little triangular with round corners. Apex: round. Margin: entire and weakly undulate. Base: broadly ovate. Length: about 30 to 40 mm. Width: about 30 to 40 mm. Texture: Upper surface: smooth and satiny. Under surface: smooth and satiny. Color (when fully opened) upper surface: red/purple (RHS 58A). Outer edges and spots are yellow/green (RHS 145D). Under surface: main color is yellow/green (RHS 145D) with red/purple spots (RHS 58A). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex of midlobe and lateral lobes: oval. Length midlobe: about 18 mm. Width (not flattened) midlobe: about 21 mm. Length lateral lobes (not flattened): about 18 mm. Width (not flattened) lateral lobes: about 15 mm. Depth of tube created by lateral lobes of labellum: about 15 mm. Texture: Upper & under surface: smooth and satiny. Color (when fully opened): Midlobe: upper surface: red/purple (RHS 61A). On top a little purple (RHS N78A). In the center at the base little yellow (RHS 9A) with red/purple spots (RHS 59A). Under surface: grey/white (RHS 156D). In the center and the outer edges purple (RHS N78A). Lateral lobes: upper surface: from base white (RHS NN155D), with red/purple stripes on top (RHS 60A). From base under edge little yellow (RHS 2C), then RHS 61A which runs into N78A. Under surface: white (RHS NN155B). On upper side purple (RHS N78A). Under edge little red/purple (RHS 59A) which runs into RHS N78A. Which runs into the center into RHS N78D. Cirrhi: about 6 mm. Color: first red/purple (RHS 61A) then some white (RHS NN155A) and the tips are yellow (RHS 9B). Pestle (Callosities): Length: about 4 mm. Width (not flattened): about 4 mm. Pubescence: none. Color: yellow (RHS 9B). Sides are white (RHS NN155D) with red/purple spots (RHS 60A).

*Sepals.*—Arrangement: 3 sepals, one dorsal and two laterals. Overall shape: egg-shaped. Length: about 30 to 40 mm. Width: about 21 to 31 mm. Margin: entire and weakly undulate. Apex: oval; lateral is little pointy. Texture: Upper & under surface: smooth and satiny. Color (when fully opened): Upper surface dorsal and lateral: red/purple (RHS 58A) with yellow/green (RHS 145C). Lateral has on the bottom also some darker red/purple spots (RHS 60A). Under surface dorsal and lateral: yellow/green (RHS 145D) with RHS 145B. On the sides a purple edge (RHS N78B).

*Pedicel.*—Length: about 23 to 35 mm. Diameter: about 3 mm. Texture: glabrous and smooth. Color: from the flower white (RHS N155B) which runs into yellow/green (RHS 145B).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed or fruit.

*Column.*—Length: about 8 mm. Diameter: about 5 mm. Color: white (RHS NN155D) and purple (RHS N78A and RHS N78D and RHS 72B).

*Pollinia.*—Quantity: two. Size: about 1 mm. Color: yellow/orange (RHS 17B).

*Ovary.*—Length: about 3 mm. Diameter: about 2 mm. Color: white (RHS NN155B) with purple (RHS N70A).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'FLOR239431', as illustrated and described herein.

* * * * *